United States Patent [19]

Goldgaber et al.

[11] Patent Number: 4,912,206

[45] Date of Patent: Mar. 27, 1990

[54] CDNA CLONE ENCODING BRAIN AMYLOID OF ALZHEIMER'S DISEASE

[75] Inventors: Dmitry Y. Goldgaber, Bethesda; Michael Lerman, Rockville; D. Carleton Gajdusek, Frederick, all of Md.

[73] Assignee: The United States of America as represented by the Department of Health and Human Services, Washington, D.C.

[21] Appl. No.: 19,001

[22] Filed: Feb. 26, 1987

[51] Int. Cl.$^4$ .......................................... C07H 19/073
[52] U.S. Cl. ........................................ 536/27; 536/28; 536/29; 435/6; 530/324
[58] Field of Search ................. 536/27, 28, 29; 435/6

[56] References Cited

U.S. PATENT DOCUMENTS 4,666,829  5/1987  Glenner et al. ..................... 435/6

OTHER PUBLICATIONS

King et al., A Dictionary of Genetics, Oxford Univ. Press, New York, 1985, p. 76.
Glover, Gene Cloning, Chapman and Hall, New York, 1984, Supp. 102–104
Old et al., Principles of Gene Manipulation, Univ. of California Press, Berkeley, Calif., 1981, Supp. 104, 105, 119 & 120.
Kunisada et al., Nucleic Acids Research, vol. 14 (14), pp. 5729–5740, 1986.
Stearman et al., Nucleic Acids Research, vol. 14 (2), pp. 797–809, 1986.
Wurtman et al., *Alzheimer's Disease*: Advances in Basic Research and Therapies, Zurich, Switzerland, Jan. 16–18, 1987.
*UCLA Symposium* "Molecular Biology of Human Brain", Keystone, Colo., Apr. 20–25, 1987.
Goldgaber et al., *Science*, 235:887–880, 1987, "Characterization and Chromosomal Localization of a cDNA Encoding Brain Amyloid of Alzheimer's Disease".
Delabar et al., *Science* 235:1390–1392, 1987, "Amyloid Gene Duplication in Alzheimer's Disease and Karyotypically Normal Down Syndrome".

*Primary Examiner*—Ronald W. Griffin
*Assistant Examiner*—L. Eric Crane
*Attorney, Agent, or Firm*—Mishrilal L. Jain

[57] ABSTRACT

Four clones have been isolated from an adult human brain cDNA library using an oligonucleotide probe corresponding to the first 20 amino acids of the brain amyloid polypeptide of the Alzheimer's disease. The open reading frame of the sequenced clone coded for 97 amino acids including the known amino acid sequence of this polypeptide. The 3.5 kb messenger RNA has been detected in mammalian brains and human thymus. The gene is highly conserved in evolution and been mapped to human chromosome 21.

3 Claims, 9 Drawing Sheets

FIG. 1

```
       asp  ala  glu  phe  arg  his  asp  ser  gly  tyr
                                           T C
5'-    GAI  GCI  GAI  TTI  AGI  CAI  GAI  I    GGI  TAI
                             C         A G glu  val  his  his  gln  lys  leu  val  phe  phe
       GAI  GTI  CAI  CAI  CAI  AAI  CTI  GTI  TTI  TTI  T[T]-3'
                                        T ala  glu  asp  val  gly  ser  asn  lys
```

FIG.2

```
1                                      10
        GAA TTC CGA CAT GAC TCA GGA TAT GAA GTT CAT CAT CAA
        Glu Phe Arg His Asp Ser Gly Tyr Glu Val His His Gln
Asp Ala Glu Phe Arg His Asp Ser Gly Tyr Glu Val His His Gln 20                              28      30
AAA TTG GTG TTC TTT GCA GAA GAT GTG GGT TCA AAC AAA GGT GCA
Lys Leu Val Phe Phe Ala Glu Asp Val Gly Ser Asn Lys Gly Ala
Lys Leu Val Phe Phe Ala Glu Asp Val Gly Ser Asn Lys Gly Ala 40      42
ATC ATT GGA CTC ATG GTG GGC GGT GTT GTC ATA GCG ACA GTG ATC
Ile Ile Gly Leu Met Val Gly Gly Val Val Ile Ala Thr Val Ile
Ile Ile Gly Leu Met Val Gly Gly Val Val Ile Ala 50                                      60
GTC ATC ACC TTG GTG ATG CTG AAG AAG AAA CAG TAC ACA TCC ATT
Val Ile Thr Leu Val Met Leu Lys Lys Lys Gln Tyr Thr Ser Ile

70
CAT CAT GGT GTG GTG GAG GTT GAC GCC GCT GTC ACC CCA GAG GAG
His His Gly Val Val Glu Val Asp Ala Ala Val Thr Pro Glu Glu 80                                      90
CGC CAC CTG TCC AAG ATG CAG CAG AAC GGC TCA GAA AAT CCA ACC
Arg His Leu Ser Lys Met Gln Gln Asn Gly Ser Glu Asn Pro Thr

100
TAC AAG TTC TTT GAG CAG ATG CAG AAC TAG
Try Lys Phe Phe Glu Gln Met Gln Asn End
```

|   | 1 | 2 | 3 | 4 | 5 | 6 | 7 | 8 |

CDNA CLONE ENCODING BRAIN AMYLOID OF ALZHEIMER'S DISEASE

BACKGROUND OF THE INVENTION

1. Technical Field

The present invention is related generally to oligonucleotide probes. More particularly, the present invention is related to the isolation and cloning of a DNA sequence encoding brain β-amyloid polypeptde of Alzheimer's-disease.

2. State of the Art

Extracellular amyloid plaque cores and cerebrovascular amyloid deposits in Alzheimer's disease (AD) and adult Down's syndrome (DS), neurofibrillary tangles of Guamanian amyotrophic lateral sclerosis/Parkinsonism-dementia (ALS/PD), and amyloid of the aging brain contain the same unique amyloid polypeptide, (Glenner, et al, *Biochem. Biophys. Res. Commun.* 122,1131, (1984); Quaranta, et al, *Proc. Nat. Acad. Sci. U.S.A.* 82, 8729 (1985); Masters, et al, *EMBO J.* 4, 2757, 1985). In order to understand the origin of these neuropathological changes, it was believed that as first step a cDNA clone encoding this polypeptide should be isolated.

SUMMARY OF THE INVENTION

It is, therefore, an object of the present invention to provide cDNA clones encoding the brain amyloid polypeptide found in such disorders, as Alzheimer's disease.

Various other objects and advantages will become apparent from the Detailed Description of the Invention.

BRIEF DESCRIPTION OF DRAWINGS

These and other objects, features, and many of attendant advantages of the invention will be better understood upon a reading of the following detailed description when considered in connection with the accompanying drawings wherein:

FIG. 4 shows the predicted secondary structure of the deduced protein. The first line is the secondary structure predicted by the method of Chou & Fasman, *Ann. Rev. of Biochem.* 47, 251 (1978): o, alpha helix; V, beta sheet;—, turn. The second line is the deduced amino acid sequence in one letter code (a.a 3 through a.a 99). The third line is the secondary structure predicted by the method of Garnier, et al, *J. Mol. Biol.*, 120, 97 (1978): A, antiparallel beta sheet; P, parallel beta sheet; H, alpha helix. (B) Hydropathy analysis, Kyte, et al, *J. Mol. Biol.* 157, 105 (1982), of the deduced protein. The numbers on the x-axis indicate the position of amino acid residues. The numbers on the y axis are values of hydrophobic index. The main hydrophobic domain of the deduced amino acid sequence (a.a 29 through, a.a 52) is shown as |———| at the top of the figure. The putative cleavage site between a.a 42 and a.a 43 is shown with a broken arrow;

FIG. 6 shows the results of detection of the AD-AP gene in human-rodent somatic cell hybrid DNAs. DNA (10 μg) was cleaved with EcoRI or Hind III, size fractionated by electrophoresis in 0.7% agarose gels, transferred to nylon membranes and hybridized with a 32p-labeled 1 kb EcoRI fragment of the λAm4 clone under high stringency (i.e., less than 10% divergence allowed). After hybridization, the blots were washed in 0.3M NaCI, 0.03M sodium citrate and 0.2% sodium dodecyl sulfate at room temperature (about 22° C. -27° C.), and then in 0.015M sodium citrate. 0.2% sodium dodecyl sulfate at 55° C. Hybridization was detected by autoadiography. Hybridizing human sequence (+) were readily distinguished from homologous rodent sequences in the hybrid cell DNAs. LM, CH, and HP indicate mouse, Chinese hamster, and human placental control DNA lanes.

DETAILED DESCRIPTION OF THE INVENTION

The above and various other objects and advantages of the present invention are achieved by a cDNA clone encoding β-amyloid protein found in Alzheimer's disease.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Figure 1:
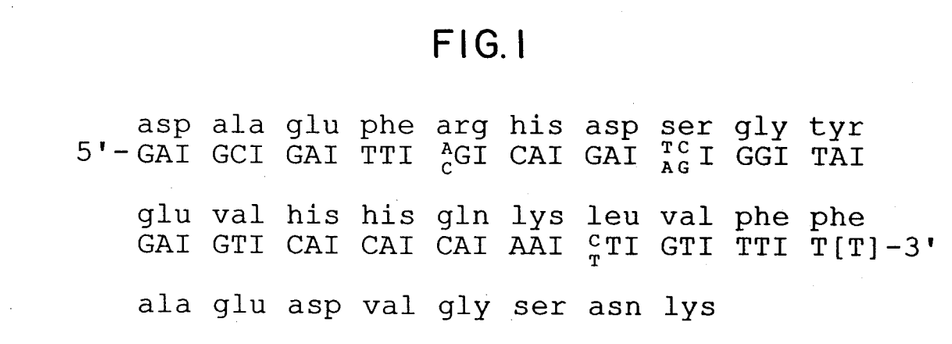
FIG. 1 represents the 59-mer oligonucleotide probe with the deoxyinosine in every third position (second line) corresponding to the first 20 amino acids of the 28 amino acid sequence (first line) for brain amyloid of Alzheimer's disease and adult Down's syndrome.

In order to prepare the cDNA clone, first the amino acid sequence of the amyloid polypeptide was analyzed with a computer to locate, that sequence of amino acids in the amyloid polypeptide which was not found in known sequences deposited in the computer banks of protein sequences. Through such analysis, it was determined that there was a sequence containing 20 amino acids in a sequence of 28 amino acids of the amyloid polypeptide which was unique and not duplicated in any other polypeptide. Based on this finding, a 59-mer oligonucleotide probe corresponding to these 20 amino acids was synthesized following standard techniques well known in the art such as Ohtsuka, et al, *J. Biol. Chem.* 260, 2605 (1985); Takahashi, et al, *Proc. Nat. Acad. Sci., U.S.A.* 82, 1931 (1985); and the 59-mer oligonucleotide was thus synthesized using deoxyinosine in every third position (FIG. 1)

Figure 2:
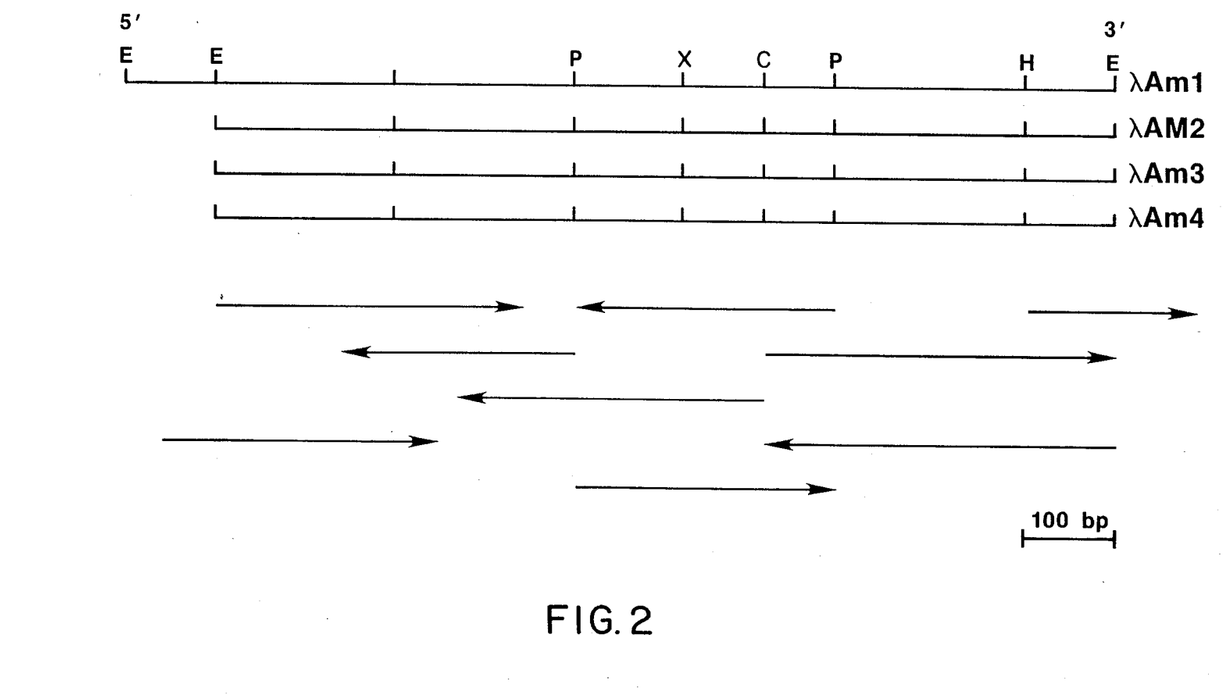
FIG. 2 shows the restriction maps of four cDNA clones (λAm1 through λAm4) isolated from adult human brain λgt 11 cDNA library; sequencing strategy of the λAm4 clone. The λAm2, λAm3, and λAm4 clones were about 1 kb; λAm1, was about 1OO bp longer and contained an internal EcoRI site. Restriction enzyme sites: E:EcoRi, P:Pvu II, C:Cla I, X:Xmn I, H:Hind III. The arrows represent pGem bl subslones, direction of sequencing, and length of sequence data derived by the chain termination method with the use of unique restriction sites for subcloning, and sequencing protocol from Promega Biotec.

By screening with the 59-mer oligonucleotide probe, four clones (λAm1–λAm4) were isolated from an adult human brain cDNA library made in a λgt 11 vector as described by Huynh, et al, *DNA Cloning.* 1, 49 (1985). The adult human brain λgt 11 cDNA library and poly (A)+ RNAs were commercially purchased from Clontech, Palo Alto, CA. Restriction maps of the four positive cDNA clones revealed that they were identical, except for one which was approximately 100 bp longer than the other three and contained an internal EcoRI site (FIG. 2).

Southern blot analysis of the λAm4 clone showed that the 59-mer probe hybridized to the EcoRI-Pvu II fragments at the 5' end of the insert. The whole 1 kb EcoRI insert of clone λAm4 was subcloned in pGEM-3 plasmid and its fragments in pGEM blue plasmid; Plasmids PGEM-3 (R) and pGEM blue (R) were purchased from Promega Biotec, Madison, WI. Dideoxy-sequencing directed from plasmid DNA was done according to Promega Biotec Technical Bulletin; and sequenced by the chain termination method of Sanger, et al, *Proc. Nat. Acad. Sci., U.S.A.* 74, 5463 (1977), (FIG. 2). The sequence contained an open reading frame which has been translated into an amino acid sequence.

Figure 3:
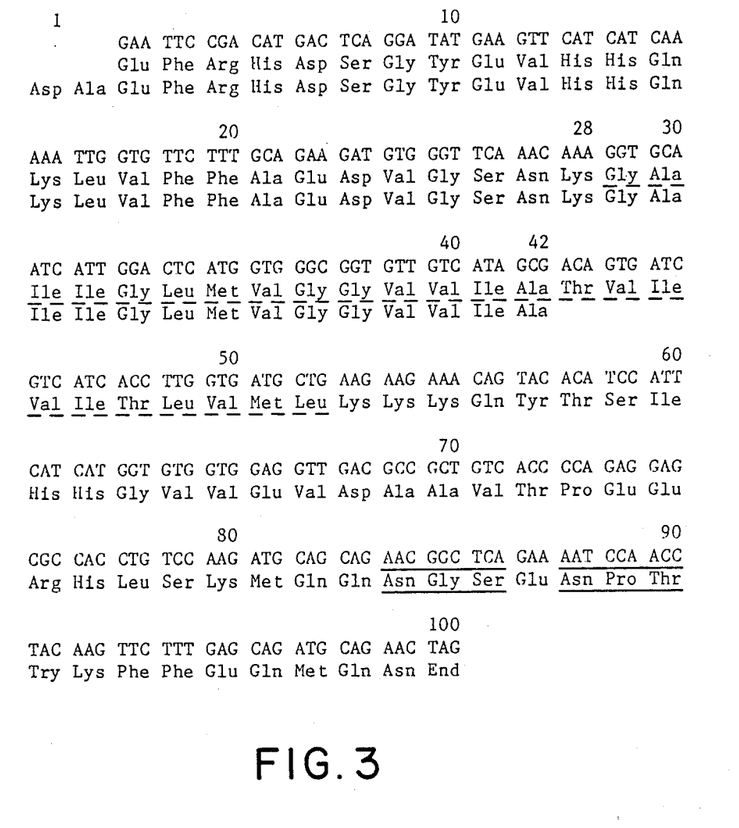
FIG. 3 represents the nucleotide sequence of the open reading frame of cDNA clone Am4 (first line) and deduced protein sequence (second line) compared with amino acid sequence for isolated amyloid polypeptide from Alzheimer's disease and Down's syndrom (third line). Numbers indicate amino acid position. End, stop codon; potential N-glycosylation sites at positions 84 and 88 are boxed, the main hydrophobic domain is underlined with a broken line.

The deduced 97 amino acid sequence from the first 291 nucleotides included the sequence foramino acid 3 to 42 of the brain amyloid polypeptide of AD and DS (Glenner, et al, *Biochem. BIohys. Res. Commun.* 122, 1131 (1984); Wong, et al, *Proc. Nat. Acad. Sci., U.S.A.* 82, 8729 (1985); Masters et al, *EMBO J.* 4, 2757 (1985); Beyreuther et al, *Disc. in Neurosci.* 3, 1 1986). Beyond the 42nd amino acid, which is the termination of all brain amyloid subunits yet isolated from AD and DS, there follow another 57 amino acids and a TAG termination codon (FIG. 3). It was determined that the nucleotide sequences of the cDNA clone and the deduced amino acid sequences described herein have no extensive homology to that of any previously known sequences, (Protein Sequence Database, National Biomedical Research Foundation, Washington, D.C.; GENBANK (R), Los Alamos National Laboratory).

Figure 4A:
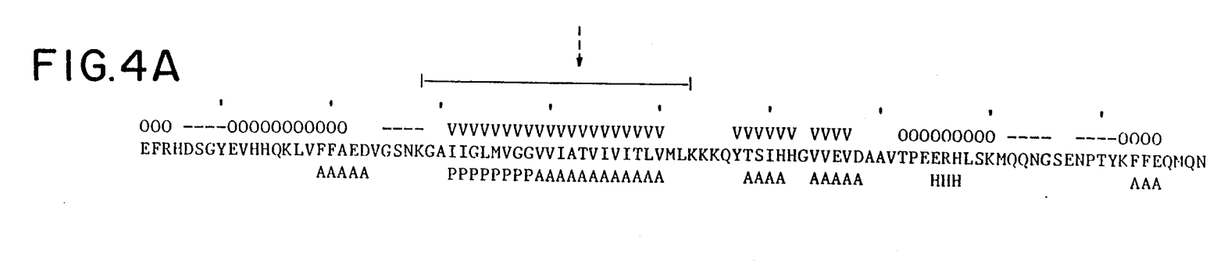
Figure 4B:
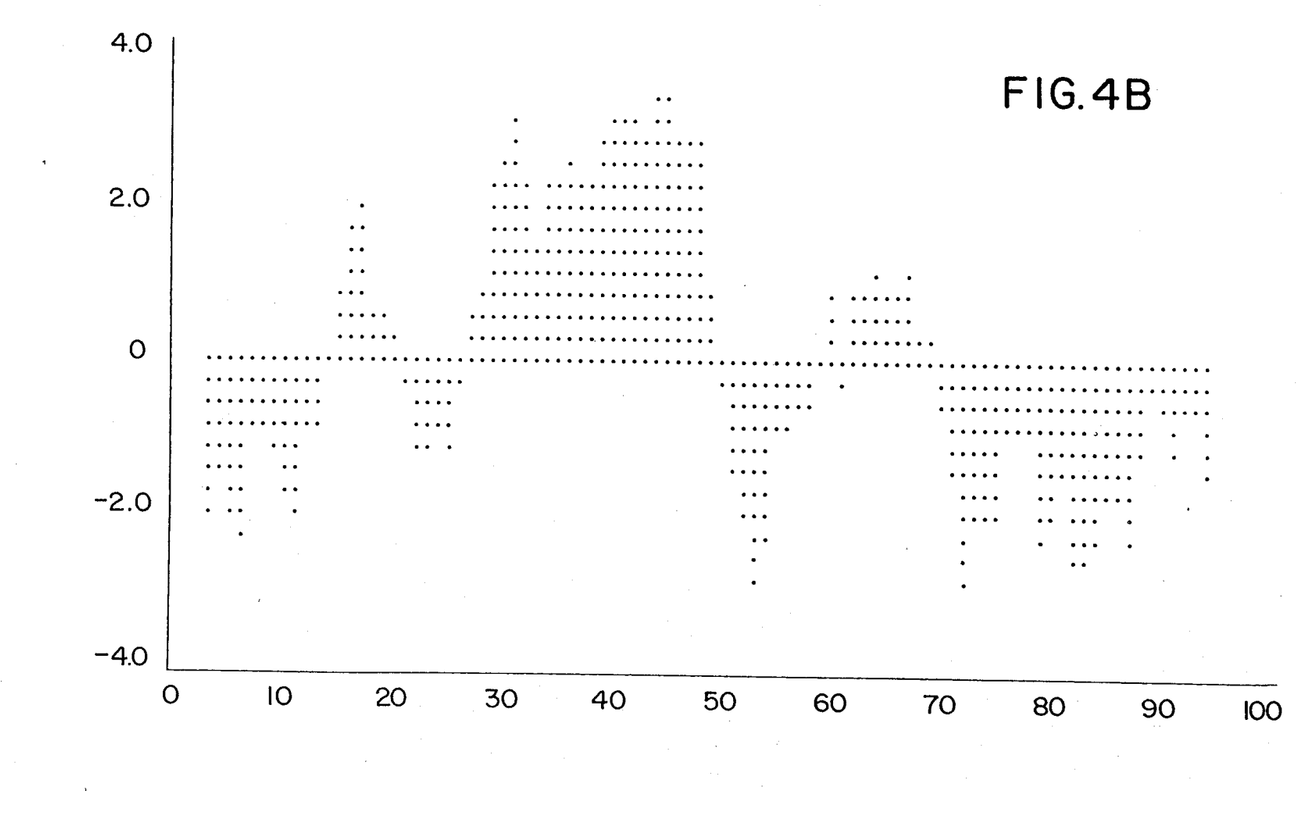

Hydropathy analysis conducted as described by Kyte, et al, *J. Mol. Biol.* 157, 105 (1982) of the deduced amino acid sequence showed a large hydrophobic domain and alternating hydrophobic and hydrophilic regions (FIG. 4B). This could have important implications for the structural organization and function of the putative protein, and possibly result in aggregate formation. Secondary structure predictions were made using the methods of Chou and Fasman, *Ann. Rev. of BIochem.* 47, 251 (1978); and Garnier, et al, *J. Mol. Biol.*, 120, 97 (1978). Strong beta-pleated sheet tendency (amino acid 31–50) was revealed in the deduced amino acid sequence (FIG. 4A) which is consistent with the known structure of amyloid (Puchtler, et al, *J. Histochem. Cytochem.* 10, 335, (1962); Glenner, *N. Engl. J. Med.* 302, 1283, 1980). In conversion of the precursor protein to amyloid, cleavage should occur between amino acid 42 and amino acid 43 which lie within the main hydrophobic domain. There are two potential N-glycosylation sites (Asn-X-Thr/Ser), at positions 84 and 88. At the present time there is no evidence that this protein is or is not glycosylation, but in any case, the second site is proline residue (FIG. 3) (Roni, et al, *FEBS Letters* 96, 179 (1978); Bause, *FEBS Letters* 103, 296, 1979). A fusion protein of 126 kDa was produced in *E. coli* Y1089. The 12 kDA recombinant part of this protein is consistent with the estimated size of the deduced polypeptide.

Figure 5:
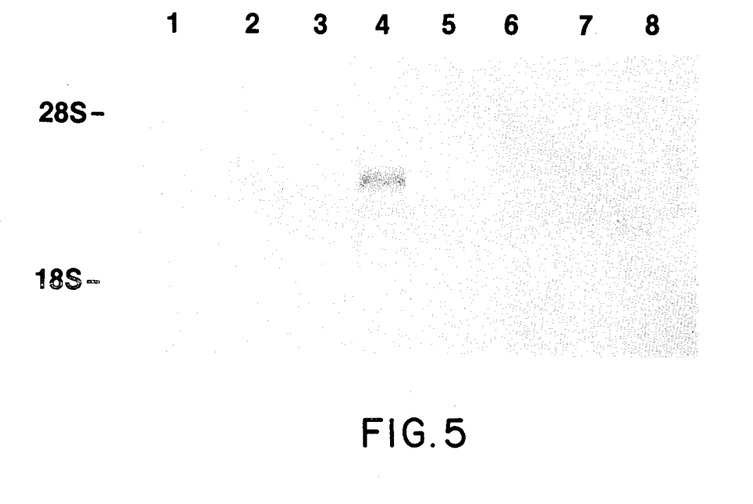
FIG. 5 shows the northern blot analysis of poly (A)+ RNA isolated from mammalian brains and various human tissues. RNA (5 μg) was electrophoresed through a 0.8% formaldehyde-agarose gel. RNA was transferred to nitrocellulose and hybridized with $^{32}$P-labeled 1 kb EcoRI fragment from λAm4 clone (specific activity=$3 \times 10^8$cpm/ug)

Northern blot analysis of poly (A)+RNA was performed according to Huynh, et al, *DNA Cloning.* 1, 49, (1985) with the 1 kb EcoRI fragment of the λAm4 clone (hereafter referred to as the λAm4 probe) under high stringencey conditions. A single band of about 3.5 kb was detected in RNA preparations from mouse, rat and cow brains and human thymus, indicating that the 1 kb cDNA represents only a fraction of the message. No bands were detected in RNA preparations from the hippocampus region of a 70 year old man, human placenta, epithelium or liver. However, this may well be due to the sensitivity limit of the Northern blot method employed (FIG. 5). The gene is thus transcriptionally active and encodes a single messenger RNA specie. The presence of the mRNA in brains of distantly related species is consistent with a conserved gene. It is not known in which cells of the brain the gene encoding the protein that forms amyloid in Alzheimer's disease (AD-AP gene) is expressed.

To chromosomally map the AD-AP gene, the DNA of 53 human-mouse and 32 human-hamster somatic cell hybrids that retained varying groups of human chromosomes after segregation, was examined. Strongly hybridizing 3.2 kb and polymorphic 9.6 kb bands in EcoRI digest of human DNA were widely separated from 2.7 kb and 5 kB homologous mouse sequences when tested with the Am4 probe (FIG. 6). The EcoRI 9.6 kb human polymorphic band was less well resolved from a single 8.5 kb homologous sequence of hamster DNA digested with the same endonuclease. Hence, Southern blot analysis of both Hind III and EcoRI digests of these hybrid cell DNAs was performed with the same probe. These anaylses were in complete agreement and permitted unambiguous assignment of all detectable human sequences to chromosome 21.

TABLE 1

| Segregation of the AD-AP Gene in Human Rodent Hybrids. | |
|---|---|
| Human Chromosome | % Discordancy |
| 1 | 53 |
| 2 | 61 |
| 3 | 36 |
| 4 | 38 |
| 5 | 52 |
| 6 | 40 |
| 7 | 39 |
| 8 | 46 |
| 9 | 60 |
| 10 | 59 |
| 11 | 55 |
| 12 | 58 |
| 13 | 47 |
| 14 | 40 |
| 15 | 38 |
| 16 | 48 |
| 17 | 45 |
| 18 | 34 |
| 19 | 45 |
| 20 | 44 |
| 21 | 1 |
| 22 | 56 |
| X | 38 |

The AD/AP gene was detected as 3.2 and 9.6 or 11 kb polymorphic bands in EcoRI digests or 1.8, 3./4 7.2 and 13.7 kb bands in Hind III digests of somatic cell hybrid DNAs after hybridization with the 1kb EcoRI fragments of the λAM4 clone. Detection of the human AD-AP sequences is correlated with the presence or absence of each human chromosome in the somatic cell hybrids. Discordancy indicates presence of the chromosome when the gene is absent or absence of the chromosome despite the presence of the gene, represents percent discordancy. The human-hamster hybrids consisted of 20 primary clones and 12 subclones (25 positive per 32 total) and human-mouse hybrids consisted of 15 primary clones and 38 subclones (35 positive per 53 total).

This assignment is based upon the fact that at least 34% discordancy of the AD-AP gene with all other human chromosomes was observed. The single discordancy with chromosome 21 represents a hybrid with undetectable human superoxide dismutase (SOD-1) activity which retained the human AD-AP gene. Hybridizing bands, unexplained by recognition sited within the λAm4 probe (FIGS. 2) were observed in digests of human DNA with EcoRI, Hind III (FIG. 6) and 6 additional restriction enzymes, Bgl I, Pst I, Pvu II, Sst I, Taq I Xba I. These results most likely indicate the presence of restriction sites within introns of the gene. No additional hybridizing human bands were observed when the stringency of hybridization and washing was reduced to allow detection of sequences diverging by 30% from the λAm4 probe sequence. This indicates that the probe is quite specific and does not detect a large family of related genes. The evolutionary conservation of part or all of the AD-AP gene in mammals was demonstrated by the detection of one or more strongly hybridizing bands with the probe on Southern blots after digesting DNAs from nonhuman primates, chimpanzee, gibbon, patas, baboon capuchin, squirrel monkey, rat, mouse, and Chinese hamster with any of several different restriction endonuclease, as illustrated in FIG. 5.

The data are consistent with the existence of a gene, highly conserved in evolution.

A deposit of the cDNA probe for the AD-AP gene has been made at the ATCC, Rockville, Maryland, under accession number ATCC 40305. This deposit shall be viably maintained for 30 years from the date of deposit or for the effective life of the patent if issued, or for a period of five (5) years from the date of last request for a sample of the deposit, whichever is longer. The Commissioner of Patents shall have access to the deposit upon request and the deposit shall be made available to the public without restriction upon issuance of a patent, of course, consistent with the applicable provisions of the law.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A clone of cDNA consisting essentially of a gene for encoding beta-amyloid polypeptide of Alzheimer's disease, said polypeptide including an amino acid sequence of asp ala glu phe arg his asp ser gly tyr glu val his his gln lys leu val phe phe ala ,glu asp val gly ser asn lys wherein said gene has a nucleotide sequence of 5'- GAI GCI GAI TTI $\frac{A}{C}$ GI CAI GAI $\frac{TC}{AG}$ I GGI TAI GAI GTI CAI CAI AAI $\frac{C}{T}$ TI

GTI, TTI T-3'.

2. The clone of cDNA of claim 1 wherein said clone is ATCC 40305.

3. The clone of cDNA of claim 2 having a reading frame as illustrated in the following sequence map:

```
1                           10
     GAA TTC CGA CAT GAC TCA GGA TAT GAA GTT
         Glu Phe Arg His Asp Ser Gly Tyr Glu Val
Asp Ala Glu Phe Arg His Asp Ser Gly Tyr Glu Val

20
     CAT CAT CAA AAA TTG GTG TTC TTT GCA GAA
     His His Gln Lys Leu Val Phe Phe Ala Glu
     His His Gln Lys Leu Val Phe Phe Ala Glu 28      30
     GAT GTG GGT TCA AAC AAA GGT GCA ATC ATT
     Asp Val Gly Ser Asn Lys Gly Ala Ile Ile
     Asp Val Gly Ser Asn Lys Gly Ala Ile Ile 40      42
     GGA CTC ATG GTG GGC GGT GTT CTC ATA GCG
     Gly Leu Met Val Gly Gly Val Val Ile Ala
     Gly Leu Met Val Gly Gly Val Val Ile Ala

50
     ACA GTG ATC GTC ATC ACC TTG GTG ATG CTG
     Thr Val Ile Val Ile Thr Leu Val Met Leu

60
     AAG AAG AAA CAG TAC ACA TCC ATT CAT CAT
     Lys Lys Lys Gln Tyr Thr Ser Ile His His

70
     GGT GTG GTG GAG GTT GAC GCC GCT GTC ACC
     Gly Val Val Glu Val Asp Ala Ala Val Thr

80
     CCA GAG GAG CGC CAC CTG TCC AAG ATG CAG CAG
     Pro Glu Glu Arg His Leu Ser Lys Met Gln Gln

90
     AAC GGC TCA GAA AAT CCA ACC
     Asn Gly Ser  Glu  Asn Pro Thr

100
     TAC AAG TTC TTT GAG CAG ATG CAG AAC TAG
     Try Lys Phe Phe Glu Gln Met Gln Asn End
```

* * * * *